United States Patent
Gill et al.

(10) Patent No.: US 11,833,149 B2
(45) Date of Patent: *Dec. 5, 2023

(54) PULSE DOSING REGIMEN AND METHODS OF TREATMENT

(71) Applicant: OSI Pharmaceuticals, LLC, Northbrook, IL (US)

(72) Inventors: Stanley C. Gill, Boulder, CO (US); Kenneth K. Iwata, Northbrook, IL (US); Gregory J. Riely, New York, NY (US); Jun Wu, Buffalo Grove, IL (US); Helena Yu, New York, NY (US)

(73) Assignee: OSI Pharmaceuticals, LLC, Northbrook, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/572,491

(22) Filed: Jan. 10, 2022

(65) Prior Publication Data

US 2022/0133725 A1 May 5, 2022

Related U.S. Application Data

(63) Continuation of application No. 16/751,288, filed on Jan. 24, 2020, now Pat. No. 11,253,520, which is a continuation of application No. 15/081,273, filed on Mar. 25, 2016, now Pat. No. 10,583,142.

(51) Int. Cl.
| | | |
|---|---|---|
| *A61K 31/517* | (2006.01) | |
| *A61K 45/06* | (2006.01) | |
| *A61K 9/51* | (2006.01) | |

(52) U.S. Cl.
CPC .......... *A61K 31/517* (2013.01); *A61K 9/5161* (2013.01); *A61K 45/06* (2013.01)

(58) Field of Classification Search
CPC ..... A61K 31/517; A61K 45/06; A61K 9/5161
See application file for complete search history.

(56) References Cited

U.S. PATENT DOCUMENTS

| | | | |
|---|---|---|---|
| 10,583,142 B2 * | 3/2020 | Gill | A61K 31/517 |
| 11,253,520 B2 * | 2/2022 | Gill | A61K 31/517 |
| 2014/0066465 A1 | 3/2014 | Stark et al. | |

FOREIGN PATENT DOCUMENTS

| | | |
|---|---|---|
| WO | 2008/127659 A2 | 10/2008 |
| WO | 2014/140989 A2 | 9/2014 |

OTHER PUBLICATIONS

Hyeon Gyu Yi, et al, Epidermal Growth Factor Receptor (EGFR) Tyrosine Kinase Inhibitors (TKIs) Are Effective for Leptomeningeal Metastasis from Non-Small Cell Lung Cancer Patients with Sensitive EGFR Mutation or Other Predictive Factors of Good Response for EGFR TKI, 65 Lung Cancer 80 (Year: 2009).*

Christian Grommes, et al, "Pulsatile" High-Dose Weekly Erlotinib for CNS Metastases from EGFR Mutant Non-Small Cell Lung Cancer, 13 Neuro-Oncology 1364 (Year: 2011).*

Jasmine Foo, et al, Effects of Pharmacokinetic Processes and Varied Dosing Schedules on the Dynamics of Acquired Resistance to Erlotinib in EGFR—Mutant Lung Cancer, 7 J Thoracic Oncol. 1583 (Year: 2012).*

J.L. Kuiper & E.F. Smit, High-Dose, Pulsatile Erlotinib in Two NSCLC Patients with Leptomeningeal Metastases—One with a Remarkable Thoracic Response As Well, 80 Lung Cancer 102 (Year: 2013).*

Shigeki Nanjo, et al, High Efficacy of Third Generation EGFR Inhibitor AZD9291 in a Leptomeningal Carcinomatosis Model with EGFR—Mutant Lung Cancer Cells, 7 Oncotarget 3847 (Year: 2015).*

ClinicalTrials.gov, Low Dose Daily Erlotinib in Combination With High Dose Twice Weekly Erlotinib in Patients with EGFR—Mutant Lung Cancer. Identifier: NCT01967095. NIH, retrieved online at: <https://clinicaltrials.gov/ct2/show/study/NCT01967095>. 8 pages, Nov. 13, 2018.

Foo et al., Effects of pharmacokinetic processes and varied dosing schedules on the dynamics of acquired resistance to erlotinib in EGFR—mutant lung cancer. J Thorac Oncol. 2012;1583-93.

Grommes et al., "Pulsatile" high-dose weekly erlotinib for CNS mesastases from EGFR mutant non-small cell lung cancer. Neuro-Oncology. Aug. 2011; 13(12):1364-69.

Kuiper et al., High-dose pulsatile erlotinib in two NSCLC patients with leptomeningeal metastases—One with a remarkable thoracic response as well. Lung Cancer. 2013; 80:102-105.

Milton et al., A phase I/II study of weekly high-dose erlotinib in previously treated patients with nonsmall cell lung cancer. Cancer. Sep. 2006;107(5):1034-41.

(Continued)

*Primary Examiner* — Sean M Basquill
(74) *Attorney, Agent, or Firm* — McCarter & English, LLP; Maria Laccotripe Zacharakis; Yelena Margolin

(57) ABSTRACT

A novel dosing regimen for erlotinib or a pharmaceutically acceptable salt thereof is described herein. The dosing regimen demonstrates impressive control of central nervous system disease, which is better than that reported with standard dose erlotinib. The use of the novel dosing regimen for treating patients in need thereof, including for controlling formation of metastatic brain, leptomeninges, or CNS lesions in a patient with non-small cell lung cancer (NSCLC) that harbors epidermal growth factor receptor (EGFR) mutation with or without pre-existing brain metastases, is also described herein.

29 Claims, 5 Drawing Sheets

(56) References Cited

OTHER PUBLICATIONS

Pastorino et al., Cerebrospinal fluid pharmacokinetics and pharmacodynamics following high-dose erlotinib treatment in brain cancer patients. Cancer Research. 2014;74, Abstract No. 4652. 1 page.
Yi et al., Epidermal growth factor receptor (EGFR) tyrosine kinase inhibitors (TKIs) are effective for leptomeningeal metastasis from non-small cell lung cancer patients with sensitive EGFR mutation or other predictive factors of good response for EGFR TKI. Lung Cancer. 2009; 65:80-84.
Yu et al., A phase I study of twice weekly pulse dose and daily low dose erlotinib as initial treatment for patients (pts) with EGFR-mutant lung cancers. Journal of Clinical Oncology. 2015;15, Abstract No. 8017. 2 pages.
International Search Report and Written Opinion for Application No. PCT/US2016/024232, dated Jul. 11, 2016, 17 pages.
U.S. Appl. No. 15/081,273, filed Mar. 25, 2016, U.S. Pat. No. 10,583,142, Mar. 10, 2020.
U.S. Appl. No. 16/751,288, filed Jan. 24, 2020, U.S. Pat. No. 11,253,520, Feb. 22, 2022.

\* cited by examiner

PULSE DOSING REGIMEN AND METHODS OF TREATMENT

RELATED APPLICATIONS

This Application is a continuation of U.S. patent application Ser. No. 16/751,288, filed on Jan. 24, 2020; which is a continuation of U.S. patent application Ser. No. 15/081,273, filed on Mar. 25, 2016, now U.S. Pat. No. 10,583,142, issued on Mar. 10, 2020. The entire contents of each of the foregoing applications are hereby incorporated herein by reference.

FIELD OF THE INVENTION

The present disclosure describes a novel dosing regimen for erlotinib or a pharmaceutically acceptable salt thereof. The dosing regimen demonstrates impressive control of central nervous system disease, which is better than that reported with standard dose erlotinib. The present disclosure describes the use of the novel dosing regimen for treating patients in need thereof, including for controlling formation of metastatic brain, leptomeninges, or CNS lesions in a patient with non-small cell lung cancer (NSCLC) that harbors epidermal growth factor receptor (EGFR) mutation with or without pre-existing brain, leptomeninges, or CNS metastases.

BACKGROUND OF THE INVENTION

TARCEVA® (erlotinib HCl) is a tyrosine kinase inhibitor (TKI). As referenced in the FDA-approved label, TARCEVA® is indicated in the United States for first-line treatment of patients with metastatic non-small cell lung cancer (NSCLC) whose tumors have epidermal growth factor receptor (EGFR) exon 19 deletions or exon 21 (L858R) substitution mutations as detected by an FDA-approved test; maintenance treatment of patients with locally advanced or metastatic NSCLC whose disease has not progressed after four cycles of platinum based first-line chemotherapy; treatment of locally advanced or metastatic NSCLC after failure of at least one prior chemotherapy regimen; and first-line treatment of patients with locally advanced, unresectable or metastatic pancreatic cancer, in combination with gemcitabine.

TARCEVA® (erlotinib), a tyrosine kinase inhibitor, is a quinazolinamine with the chemical name N-(3-ethynylphenyl)-6,7-bis(2-methoxyethoxy)-4-quinazolinamine. TARCEVA® contains erlotinib as the hydrochloride salt that has the following structural formula:

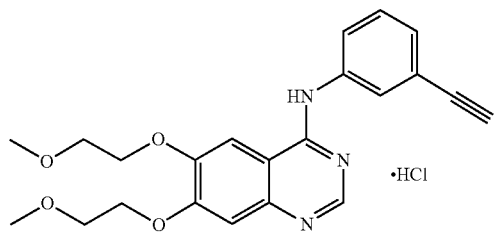 [SMILES: C#Cc1cccc(Nc2ncnc3cc(OCCOC)c(OCCOC)cc23)c1 ; Cl]

Reference is made to U.S. RE 41,065, herein incorporated by reference with regard to the description and synthesis of the compound.

Erlotinib hydrochloride has the molecular formula $C_{22}H_{23}N_3O_4 \cdot HCl$ and a molecular weight of 429.90. The molecule has a pKa of 5.42 at 25° C. Erlotinib hydrochloride is very slightly soluble in water, slightly soluble in methanol and practically insoluble in acetonitrile, acetone, ethyl acetate, and hexane. Aqueous solubility of erlotinib hydrochloride is dependent on pH with increased solubility at a pH of less than 5 due to protonation of the secondary amine. Over the pH range of 1.4 to 9.6, maximal solubility of approximately 0.4 mg/mL occurs at a pH of approximately 2.

Epidermal growth factor receptor (EGFR) is expressed on the cell surface of both normal and cancer cells. In some tumor cells signaling through this receptor plays a role in tumor cell survival and proliferation irrespective of EGFR mutation status. Erlotinib reversibly inhibits the kinase activity of EGFR, preventing autophosphorylation of tyrosine residues associated with the receptor and thereby inhibiting further downstream signaling. Erlotinib binding affinity for EGFR exon 19 deletion or exon 21 (L858R) mutations is higher than its affinity for the wild type receptor. Erlotinib inhibition of other tyrosine kinase receptors has not been fully characterized.

As with other ATP competitive small molecule tyrosine kinase inhibitors, patients may develop resistance. Over 50% of resistance is caused by a mutation in the ATP binding pocket of the EGFR kinase domain involving substitution of a small polar threonine residue with a large nonpolar methionine residue, T790M. See, Balak et al., *Novel D761Y and common secondary T790M mutations in epidermal growth factor receptor-mutant lung adenocarcinomas with acquired resistance to kinase inhibitors*, Clin. Cancer Res 12 (1): 6494-501, (2006). While proponents of the 'gatekeeper' mutation hypothesis suggest this mutation prevents the binding of erlotinib through steric hindrance, research suggests that T790M confers an increase in ATP binding affinity, thereby reducing the inhibitory efficacy of erlotinib. See, Yun et al., *The T790M mutation in EGFR kinase causes drug resistance by increasing the affinity for ATP*, PNAS 105 (6): 2070-5, (2008).

EGFR-mutant lung cancers are highly responsive to EGFR tyrosine kinase inhibitors (TKIs) with superior progression free survival when compared to cytotoxic chemotherapy. See, for example, Lee et al., *Impact of Specific Epidermal Growth Factor Receptor (EGFR) Mutations and Clinical Characteristics on Outcomes after Treatment with EGFR Tyrosine Kinase Inhibitors Versus Chemotherapy in EGFR-Mutant Lung Cancer: A Meta-Analysis*, Journal of clinical oncology. 2015; 33(17):1958-65; Mok et al., *Gefitinib or carboplatin-paclitaxel in pulmonary adenocarcinoma*, The New England Journal of Medicine, 2009; 361 (10):947-57; Rosell et al., *Erlotinib versus standard chemotherapy as first-line treatment for European patients with advanced EGFR mutation-positive non-small-cell lung cancer (EURTAC): a multicentre, open-label, randomised phase 3 trial*, The Lancet Oncology, 2012; 13(3):239-46; and Sequist et al., *Phase III Study of Afatinib or Cisplatin Plus Pemetrexed in Patients With Metastatic Lung Adenocarcinoma With EGFR Mutations*, Journal of Clinical Oncology, 2013; 31(27):3327-34. The majority of patients will respond to erlotinib, gefitinib, and afatinib, but in less than a year develop resistance to further therapy with these agents. See, Sequist et al., *Phase III Study of Afatinib or Cisplatin Plus Pemetrexed in Patients With Metastatic Lung Adenocarcinoma With EGFR Mutations*, Journal of Clinical Oncology. 2013; 31(27):3327-34; Maemondo et al., *Gefitinib or chemotherapy for non-small-cell lung cancer with mutated EGFR*, The New England Journal of Medicine, 2010; 362(25):2380-8; Mok et al., *Gefitinib or Carboplatin-*

*Paclitaxel in Pulmonary Adenocarcinoma.* N. Engl. J. Med., 2009; 361(10):947-57; and Janne et al., *Randomized Phase II Trial of Erlotinib Alone or With Carboplatin and Paclitaxel in Patients Who Were Never or Light Former Smokers With Advanced Lung Adenocarcinoma: CALGB* 30406 *Trial*, Journal of Clinical Oncology, 2012; 39(17): 2063-9. As noted hereinabove, the most common mechanism of resistance is acquisition of an EGFR T790M mutation, identified in 60% of patients with acquired resistance to EGFR TKIs. See also, Kobayashi et al., *EGFR mutation and resistance of non-small-cell lung cancer to gefitinib*, The New England Journal of Medicine. 2005; 352(8):786-92, and Yu et al., *Analysis of tumor specimens at the time of acquired resistance to EGFR-TKI therapy in* 155 *patients with EGFR-mutant lung cancers*, Clinical Cancer Research, 2013, 19(8): 2240-7. Acquired resistance occurs, however, with the central nervous system as a frequent site of relapse. A parallel strategy to improve outcomes in patients with EGFR-mutant lung cancers is to adjust initial treatment to delay or prevent acquired resistance. While some have investigated EGFR TKIs in combination with other agents, modulating EGFR TKI dosing to prevent resistance in patients with EGFR-mutant lung cancers has not been assessed. See, Johnson et al., *Phase I/II Study of HSP90 Inhibitor AUY922 and Erlotinib for EGFR-Mutant Lung Cancer With Acquired Resistance to* 18 *Epidermal Growth Factor Receptor Tyrosine Kinase Inhibitors*, Journal of Clinical Oncology, 2015, 33(15):1666-73, Riely et al., *Prospective assessment of discontinuation and reinitiation of erlotinib or gefitinib in patients with acquired resistance to erlotinib or gefitinib followed by the addition of everolimus*, Clinical Cancer Research, 2007, 13(17):5150-5, Reguart et al., *Phase I/II trial of vorinostat (SAHA) and erlotinib for non-small cell lung cancer (NSCLC) patients with epidermal growth factor receptor (EGFR) mutations after erlotinib progression*, Lung Cancer, 2014, 84(2):161-7, Johnson et al., *Phase II trial of dasatinib for patients with acquired resistance to treatment with the epidermal growth factor receptor tyrosine kinase inhibitors erlotinib or gefitinib*, Journal of Thoracic Oncology. 2011, 6(6):1128-31, and Goldberg et al., *A phase I study of erlotinib and hydroxychloroquine in advanced non-small-cell lung cancer*, Journal of Thoracic Oncology, 2012, 7(10):1602-8. Third generation EGFR TKIs, such as osimertinib, which inhibit EGFR T790M may be effective at the time of progression on erlotinib, afatinib, or gefitinib.

Erlotinib was initially developed to inhibit wild-type EGFR. The 150 mg daily dose was the maximum tolerated dose established via a phase I study (Hildalgo et al.), which predated knowledge of EGFR mutation. The choice of a 150 mg daily dose, therefore, did not take into consideration the development of drug resistance in patients whose tumors harbor EGFR mutations. Hidalgo et al., *Phase I and pharmacologic study of OSI-774, an epidermal growth factor receptor tyrosine kinase inhibitor in patients with advanced solid malignancies*, Journal of Clinical Oncology, 2001, 19(13):3267-79. Mathematical modeling can predict the evolutionary dynamics that result in proliferation of resistant clones, and suggest potential alternative dosing schedules to delay resistance. See, Chmielecki et al., *Optimization of dosing for EGFR-mutant non-small cell lung cancer with evolutionary cancer modeling*, Science Translational Medicine, 2011, 3(90):90ra59, and Foo et al., *Evolution of resistance to targeted anti-cancer therapies during continuous and pulsed administration strategies*, PLoS Computational Biology, 2009, 5(11): e1000557. Yu et al., used these methods to evaluate different dosing schedules of erlotinib and selected twice weekly high dose of erlotinib plus daily low dose erlotinib as better able to delay progression in the setting of pre-existing resistant, EGFR T790M positive cells. The mathematical prediction and hypotheses were confirmed in pre-clinical studies using 20 μM erlotinib/1 μM erlotinib and 100 nM afatinib/1 μM erlotinib doses. See, Chmielecki et al., *Optimization of dosing for EGFR-mutant non-small cell lung cancer with evolutionary cancer modeling*, Science Translational Medicine, 2011, 3(90):90ra59.

Milton et al., conducted a study of weekly high dose erlotinib in unselected patients with advanced lung cancers. See, Milton et al., *Weekly high-dose erlotinib in patients with non-small cell lung cancer (NSCLC): a phase I/II study*, Cancer, 2006; 107(5):1034-41. The maximum tolerated dose (MTD) was not reached at erlotinib 2000 mg once weekly. A separate Phase 1 study of twice-weekly pulse dose erlotinib identified the MTD to be erlotinib 1000 mg twice-weekly, with a DLT of rash seen at higher dose levels. See, Chia et al., *A Phase* 1 *dose escalation pharmacokinetic (PK) and pharmacodynamic (PD) study of weekly and twice weekly erltoinib in advanced stage malignancies*, Journal of Clinical Oncology, 2007:25, Suppl; Abstract 3594.

Due to a wide inter-subject variability in bioavailability, lower daily doses of erlotinib may be effective with significantly less toxicity, although not proven in a randomized trial setting. Yamada et al., *A prospective, multicentre phase II trial of low-dose erlotinib in non-small cell lung cancer patients with EGFR mutations pretreated with chemotherapy: Thoracic Oncology Research Group* 0911, Eur J Cancer, 2015 September; 51(14): 1904-10; Erlotinib at a dose of 25 mg daily for non-small cell lung cancers with EGFR mutations, Journal of Thoracic Oncology, 2010; 5(7):1048-53; and Satoh et al., *Low-dose gefitinib treatment for patients with advanced non-small cell lung cancer harboring sensitive epidermal growth factor receptor mutations*. Journal of Thoracic Oncology, 2011; 6(8):1413-7.

The available data suggest that EGFR TKI high pulse dosing is tolerable and low daily dosing is effective but these have not previously been administered together in patients.

Central nervous system (CNS) involvement is a major issue for patients with EGFR-mutant lung cancers, with up to sixty percent of these patients developing brain or leptomeningeal metastases during their disease course. See, Heon et al., *The impact of initial gefitinib or erlotinib versus chemotherapy on central nervous system progression in advanced non-small cell lung cancer with EGFR mutations*, Clinical Cancer Research, 2012; 18(16):4406-14; and Omuro et al., *High incidence of disease recurrence in the brain and leptomeninges in patients with non-small cell lung carcinoma after response to gefitinib*, Cancer, 2005, 103 (11):2344-8. Although benefit is commonly seen with EGFR TKIs when CNS disease is already present, these medications inconsistently lead to durable CNS control and do not prevent the emergence of CNS metastases. Up to 33% of patients with EGFR-mutant lung cancers have CNS progression during initial EGFR TKI therapy and in a significant subset of patients, the CNS progression occurs in the setting of continued systemic control. See, Heon et al., The impact of initial gefitinib or erlotinib versus chemotherapy on central nervous system progression in advanced non-small cell lung cancer with EGFR mutations, Clinical Cancer Research, 2012, 18(16):4406-14; Omuro et al., *High incidence of disease recurrence in the brain and leptomeninges in patients with nonsmall cell lung carcinoma after response to gefitinib* Cancer, 2005; 103(11):2344-8; and Lee et al., *Frequent central nervous system failure after clinical benefit with epidermal growth factor receptor tyrosine* kinase inhibitors in Korean patients with nonsmall-cell lung cancer, Cancer, 2010, 116(5):1336-43. Central nervous system-only progression may be a result of inadequate brain penetration, with cerebrospinal fluid (CSF) concentrations of erlotinib only 3-5% of those in plasma. See, Togashi et al., *Cerebrospinal fluid concentration of erlotinib and its active metabolite OSI-420 in patients with central nervous system metastases of non-small cell lung cancer*, Journal of Thoracic Oncology, 2010, 5(7):950-5.

SUMMARY OF THE INVENTION

Consequently, the CNS becomes a common sanctuary site of disease progression due to inadequate drug delivery, not acquired drug resistance. The present inventors demonstrate that pulse dose erlotinib or a pharmaceutically acceptable salt thereof produces higher CSF concentrations and appears effective in the treatment of CNS metastases.

With erlotinib 1500 mg once weekly, a peak plasma concentration of 11,300 nM was reached with a concurrent CSF concentration of 120 nM which is above the $IC_{50}$ of erlotinib. See, Clarke et al., *High dose weekly erlotinib achieves therapeutic concentrations in CSF and is effective in leptomeningeal metastases from epidermal growth factor receptor mutant lung cancer*, Journal of Neuro-Oncology, 2010, 99(2):283-6. In an earlier series, patients with EGFR-mutant lung cancers with CNS involvement were treated with a median dose of erlotinib 1500 mg once weekly. Six of nine had a partial response in the CNS. See, Grommes et al., *"Pulsatile" high-dose weekly erlotinib for CNS metastases from EGFR mutant non-small cell lung cancer*, Neuro-Oncology, 2011, 13(12):1364-9.

One embodiment of the present disclosure includes a dosing regimen comprising: (i) orally administering one or more daily low dose of erlotinib or a pharmaceutically acceptable salt thereof; and (ii) orally administering one or more weekly high dose of erlotinib or a pharmaceutically acceptable salt thereof. One aspect of the embodiment includes a low dose of 50 mg of erlotinib or a pharmaceutically acceptable salt thereof. One aspect of the embodiment includes a high dose from about 600 mg to about 1350 mg of erlotinib or a pharmaceutically acceptable salt thereof. One aspect of the embodiment includes a high dose of 1200 mg of erlotinib or a pharmaceutically acceptable salt thereof. One aspect of the embodiment includes wherein the daily dose is once daily. One aspect of the embodiment includes wherein the weekly dose is once or twice weekly. One aspect of the embodiment includes wherein the regimen improves tolerability over a standard 100 mg to 150 mg daily dose of erlotinib or a pharmaceutically acceptable salt thereof. One aspect of the embodiment includes wherein the improved tolerability is manifested by a lower incidence in one or more of rash, diarrhea, nausea, fatigue, or mucositis.

One embodiment of the present disclosure includes a weekly dosing regimen comprising: (i) orally administering one or more pulse dose of erlotinib or a pharmaceutically acceptable salt thereof; and (ii) orally administering one or more daily dose of erlotinib or a pharmaceutically acceptable salt thereof. One aspect of the embodiment includes wherein the pulse dose is administered once daily on each of days 1 and 2 of a weekly dosing schedule. One aspect of the embodiment includes wherein the daily dose is administered once daily on each of days 3 to 7 of a weekly dosing schedule. One aspect of the embodiment includes wherein the pulse dose is from about 600 mg to about 1350 mg of erlotinib or a pharmaceutically acceptable salt thereof. One aspect of the embodiment includes wherein the pulse dose is 1200 mg erlotinib or a pharmaceutically acceptable salt thereof. One aspect of the embodiment includes wherein the daily dose is from about 25 mg to about 50 mg of erlotinib or a pharmaceutically acceptable salt thereof. One aspect of the embodiment includes wherein the daily dose is 50 mg erlotinib or a pharmaceutically acceptable salt thereof.

One embodiment of the present disclosure includes a dosing regimen of erlotinib or a pharmaceutically acceptable salt thereof comprising: (i) administering to a patient in need thereof erlotinib or a pharmaceutically acceptable salt thereof in amounts that provide a steady state concentration ($C_{trough}$) of 0.05-10 µM in the patient; and (ii) administering to a patient in need thereof erlotinib or a pharmaceutically acceptable salt thereof in amounts that provide a pulsed concentration ($C_{max}$) of 5-50 µM in the patient. One aspect of the embodiment includes wherein the steady state concentration ($C_{trough}$) is approximately 0.5 µM. One aspect of the embodiment includes wherein the pulsed concentration ($C_{max}$) is approximately 20 µM. One aspect of the embodiment includes wherein the pulsed concentration is maintained for 4 hours.

One embodiment of the present invention includes a method of treating or preventing central nervous system (CNS) metastases in a patient in need thereof comprising: (i) orally administering one or more pulse dose of erlotinib or a pharmaceutically acceptable salt thereof; and (ii) orally administering one or more daily dose of erlotinib or a pharmaceutically acceptable salt thereof. One aspect of the embodiment includes wherein the CNS metastases is leptomeningeal carcinomatosis. One aspect of the embodiment includes wherein the patient has extra-cranial metastatic non-small cell lung cancer. One aspect of the embodiment includes wherein the pulse dose is administered once daily on each of days 1 and 2 of a weekly dosing schedule. One aspect of the embodiment includes wherein the daily dose is administered once daily on each of days 3 to 7 of a weekly dosing schedule. One aspect of the embodiment includes wherein the pulse dose is from about 600 mg to about 1350 mg of erlotinib or a pharmaceutically acceptable salt thereof. One aspect of the embodiment includes wherein the pulse dose is 1200 mg erlotinib or a pharmaceutically acceptable salt thereof. One aspect of the embodiment includes wherein the daily dose is from about 25 mg to about 50 mg of erlotinib or a pharmaceutically acceptable salt thereof. One aspect of the embodiment includes wherein the daily dose is 50 mg erlotinib or a pharmaceutically acceptable salt thereof. One aspect of the embodiment includes wherein the patient with or without pre-existing brain, leptomeninges, or CNS metastases has no progression. One aspect of the embodiment includes wherein the patient's cerebrospinal fluid (CSF) is cleared of malignant cells. One aspect of the embodiment includes wherein the patient achieves a clinical benefit. One aspect of the embodiment includes wherein the clinical benefit is one or more of decrease in tumor size, suppression of tumor growth, delayed time to progression in CNS, unobservable increase in size of brain, leptomeninges, or CNS metastases or lesions, unobservable new brain, leptomeninges, or CNS metastases or lesion, delay in time from surgery to recurrence, increase in treatment options, delay or decrease in leptomeningeal seeding in the CSF, or an ability to delay whole brain radiation.

One embodiment of the present disclosure includes a method for controlling formation of metastatic brain, leptomeninges, or CNS lesions in a patient with non-small cell lung cancer (NSCLC) that harbors epidermal growth factor receptor (EGFR) mutation with or without pre-existing brain, leptomeninges, or CNS metastases comprising: (i)

orally administering one or more pulse dose of erlotinib or a pharmaceutically acceptable salt thereof; and (ii) orally administering one or more daily dose of erlotinib or a pharmaceutically acceptable salt thereof. One aspect of the embodiment includes wherein the pulse dose is administered once daily on each of days 1 and 2 of a weekly dosing schedule. One aspect of the embodiment includes wherein the daily dose is administered once daily on each of days 3 to 7 of a weekly dosing schedule. One aspect of the embodiment includes wherein the pulse dose is from about 600 mg to about 1350 mg of erlotinib or a pharmaceutically acceptable salt thereof. One aspect of the embodiment includes wherein the pulse dose is 1200 mg erlotinib or a pharmaceutically acceptable salt thereof. One aspect of the embodiment includes wherein the daily dose is from about 25 mg to about 50 mg of erlotinib or a pharmaceutically acceptable salt thereof. One aspect of the embodiment includes wherein the daily dose is 50 mg erlotinib or a pharmaceutically acceptable salt thereof. One aspect of the embodiment includes wherein the patient experiences no tumor formation in the central nervous system. One aspect of the embodiment includes wherein the patient's cerebrospinal fluid is cleared of malignant cells. One aspect of the embodiment includes wherein the patient achieves an objective or complete response or disease control. One aspect of the embodiment includes wherein the control is durable.

One embodiment of the present disclosure includes a combination comprising: (a) erlotinib or a pharmaceutically acceptable salt thereof (i) orally administered in one or more pulse dose of erlotinib or a pharmaceutically acceptable salt thereof; and (ii) orally administered in one or more daily dose of erlotinib or a pharmaceutically acceptable salt thereof; and (b) one or more therapeutic compounds administered in an effective amount thereof. One aspect of the embodiment includes wherein the one or more therapeutic compounds are one or more oncology therapeutic compounds. One aspect of the embodiment includes wherein the one or more therapeutic compounds are one or more inhibitors of epidermal growth factor receptor (EGFR). One aspect of the embodiment includes wherein the one or more therapeutic compounds are one or more inhibitors of EGFR is a mutant-selective inhibitor of EGFR. One aspect of the embodiment includes wherein the one or more therapeutic compounds are selected from one or more of rociletinib (CO-1686), osimertinib (AZD9291), HM61713, BI 1482694, or other third or later generation EGFR TKI. One aspect of the embodiment includes wherein the pulse dose of erlotinib or a pharmaceutically acceptable salt thereof is administered once daily on each of days 1 and 2 of a weekly dosing schedule. One aspect of the embodiment includes wherein the daily dose of erlotinib or a pharmaceutically acceptable salt thereof is administered once daily on each of days 3 to 7 of a weekly dosing schedule. One aspect of the embodiment includes wherein the pulse dose is from about 600 mg to about 1350 mg of erlotinib or a pharmaceutically acceptable salt thereof. One aspect of the embodiment includes wherein the pulse dose is 1200 mg erlotinib or a pharmaceutically acceptable salt thereof. One aspect of the embodiment includes wherein the daily dose is from about 25 mg to about 50 mg of erlotinib or a pharmaceutically acceptable salt thereof. One aspect of the embodiment includes wherein the daily dose is 50 mg erlotinib or a pharmaceutically acceptable salt thereof. One aspect of the embodiment includes wherein each dose is selected from a solid or liquid form. One aspect of the embodiment includes wherein a solid form comprises one or more of erlotinib or the one or more therapeutic compounds complexed with a cyclodextrin and nano-encapsulated into a pharmaceutically acceptable carrier.

One embodiment of the present disclosure includes a unit dose of erlotinib or a pharmaceutically acceptable salt thereof, comprising a pharmaceutical composition comprising erotinib or a pharmaceutically acceptable salt thereof which achieves a peak concentration ($C_{max}$) of 5-50 µM in a patient. One aspect of the embodiment includes wherein the unit dose is from about 600 mg to about 1350 mg of erlotinib or a pharmaceutically acceptable salt thereof. One aspect of the embodiment includes wherein the unit dose is about 1200 mg erlotinib or a pharmaceutically acceptable salt thereof. One aspect of the embodiment includes wherein the peak concentration ($C_{max}$) is approximately 20 µM. One aspect of the embodiment includes wherein the peak concentration is maintained for 4 hours. One aspect of the embodiment includes wherein the dose is selected from a solid or liquid form. One aspect of the embodiment wherein the solid form comprises erlotinib complexed with a cyclodextrin and nano-encapsulated into a pharmaceutically acceptable carrier.

One embodiment of the present disclosure includes a method of treating brain, leptomeninges, or CNS metastases in a patient diagnosed with EGFR-mutant lung cancer comprising: (i) orally administering one or more pulse dose of erlotinib or a pharmaceutically acceptable salt thereof; and (ii) orally administering one or more daily dose of erlotinib or a pharmaceutically acceptable salt thereof. One aspect of the embodiment includes wherein erlotinib or a pharmaceutically acceptable salt thereof is administered once daily on each of days 1 and 2 of a weekly dosing schedule. One aspect of the embodiment includes wherein the daily dose of erlotinib or a pharmaceutically acceptable salt thereof is administered once daily on each of days 3 to 7 of a weekly dosing schedule. One aspect of the embodiment includes wherein the pulse dose is from about 600 mg to about 1350 mg of erlotinib or a pharmaceutically acceptable salt thereof. One aspect of the embodiment includes wherein the pulse dose is 1200 mg erlotinib or a pharmaceutically acceptable salt thereof. One aspect of the embodiment includes wherein the daily dose is from about 25 mg to about 50 mg of erlotinib or a pharmaceutically acceptable salt thereof. One aspect of the embodiment includes wherein the daily dose is 50 mg erlotinib or a pharmaceutically acceptable salt thereof.

One embodiment includes a method of treating a patient diagnosed with gliablastoma comprising: orally administering one or more pulse dose of erlotinib or a pharmaceutically acceptable salt thereof; and orally administering one or more daily dose of erlotinib or a pharmaceutically acceptable salt thereof. In one aspect, the method includes wherein the pulse dose of erlotinib or a pharmaceutically acceptable salt thereof is administered once daily on each of days 1 and 2 of a weekly dosing schedule. In one aspect, the method includes wherein the daily dose of erlotinib or a pharmaceutically acceptable salt thereof is administered once daily on each of days 3 to 7 of a weekly dosing schedule. In one aspect, the method includes wherein the pulse dose is from about 600 mg to about 1350 mg of erlotinib or a pharmaceutically acceptable salt thereof. In one aspect, the method includes wherein the pulse dose is 1200 mg erlotinib or a pharmaceutically acceptable salt thereof. In one aspect, the method includes wherein the daily dose is from about 25 mg to about 50 mg of erlotinib or a pharmaceutically acceptable salt thereof. In one aspect, the method includes wherein the daily dose is 50 mg erlotinib or a pharmaceutically acceptable salt thereof.

Glioblastoma multiforme (GBM) is the most common brain tumour and has the worst prognosis. Epidermal growth factor receptor (EGFR) gene amplification, mutation and re-arrangement (all of which enhance tumor growth, survival, progression, and resistance to therapy) are frequently observed in primary GBM. The most common EGFR variant in GBM, the EGFRvIII, is characterized by a deletion of 267 amino acids in the extracellular domain, leading to a receptor which is unable to bind ligand yet is constitutively active. Epidermal growth factor receptor (EGFR) and EGFRvIII analysis is of current interest in glioblastoma. See, e.g., Gan et al., *The Epidermal Growth Factor Receptor Variant III (EGFRvIII): Where the Wild Things are Altered*, FEBS J, 2013 November, 280(21): 5350-70; Gan et al., *The EGFRvIII Variant in Glioblastoma Multiforme*, J. Clin. Neurosci., 2009 June, 16(6): 748-54; Padfield et al., *Current Therapeutics Advances Targeting EGFR and EGFRvIII in Glioblastoma*, Front. Oncol., v. 5, published online 2015 Jan. 29; and Iwata et al., *Inhibition of mutant EGFRvIII transformed cells by tyrosine kinase inhibitor OSI-774 (Tarceva)* [Abstract No. 79]. Proc. ASCO2002; 21.

The scope of the present invention includes all combinations of aspects and embodiments.

DETAILED DESCRIPTION

Figure 1:
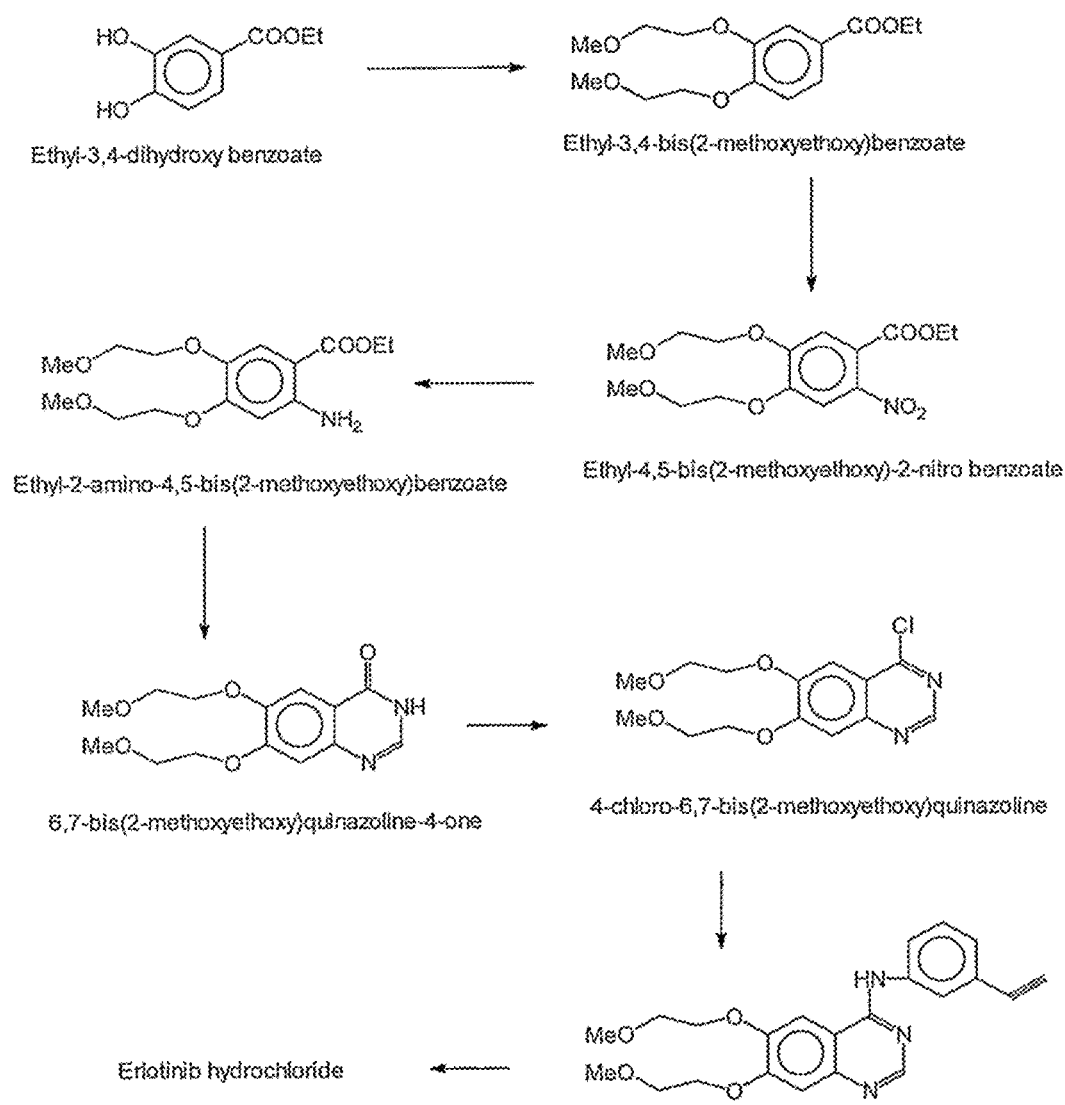
FIG. 1 illustrates a synthetic scheme for the manufacture of erlotinib.

The following definitions are meant to clarify, but not limit, the terms defined. If a particular term used herein is not specifically defined, such term should not be considered indefinite. Rather, terms are used within their accepted meanings.

As referenced herein, one embodiment of the present disclosure includes a dosing regimen comprising: (i) orally administering one or more daily low dose of erlotinib or a pharmaceutically acceptable salt thereof; and (ii) orally administering one or more weekly high dose of erlotinib or a pharmaceutically acceptable salt thereof. As used herein, the terms "low dose" and "high dose" are used relative to the other as well as relative to a standard 100 mg to 150 mg daily dose of erlotinib or a pharmaceutically acceptable salt thereof. A low dose is lower than each of the standard dose and the high dose. Likewise, a high dose is higher than each of the standard dose and the low dose. One aspect of the embodiment includes a low dose of 50 mg of erlotinib or a pharmaceutically acceptable salt thereof. One aspect of the embodiment includes a high dose from about 600 mg to about 1350 mg of erlotinib or a pharmaceutically acceptable salt thereof. One aspect of the embodiment includes a high dose of 1200 mg of erlotinib or a pharmaceutically acceptable salt thereof.

As referenced herein, one embodiment of the present disclosure includes a weekly dosing regimen comprising: (i) orally administering one or more pulse dose of erlotinib or a pharmaceutically acceptable salt thereof; and (ii) orally administering one or more daily dose of erlotinib or a pharmaceutically acceptable salt thereof. As used herein, the term "pulse dose" refers to a higher dose of erlotinib or a pharmaceutically acceptable salt thereof as compared to the daily dose. The term "pulse dose," as used herein may be determined by determining a dose that provides higher CSF concentrations than a standard 100 mg to 150 mg daily dose of erlotinib or a pharmaceutically acceptable salt thereof. One aspect of the embodiment includes wherein the pulse dose is from about 600 mg to about 1350 mg of erlotinib or a pharmaceutically acceptable salt thereof. One aspect of the embodiment includes wherein the pulse dose is 1200 mg erlotinib or a pharmaceutically acceptable salt thereof.

As used herein, the term "unit dose" refers to a dose of medicine in an individual packet for convenience, safety, or monitoring.

As used herein, the term "tolerability" refers to the degree to which overt adverse effects of a drug can be tolerated by a patient. Tolerability of a particular drug can be discussed in a general sense, or it can be a quantifiable measurement as part of a clinical study. As one measure, tolerability may be determined by the rate of dropouts, or patients that forfeit participation in a clinical study due to one or more adverse effects.

As used herein, the term "pharmaceutically acceptable" refers to carrier(s), diluent(s), excipient(s) or salt forms of the compounds of the present invention that are compatible with the other ingredients of the formulation and not deleterious to the recipient of the pharmaceutical composition.

As used herein, the terms "effective amount", "therapeutic amount", and "effective dose" refer to an amount of the compound of the present invention sufficient to elicit a desired pharmacological or therapeutic effect. Moreover, the therapeutic amount of effective amount may thus result in an effective treatment of a disorder.

Treatment of a disorder may be manifested by delaying or preventing the onset or progression of the disorder, as well as the onset or progression of symptoms associated with the disorder. Treatment of a disorder may also be manifested by a decrease or elimination of symptoms, reversal of the progression of the disorder, as well as any other contribution to the well-being of the patient.

Erlotinib may exist in free form or, where appropriate, as a pharmaceutically acceptable derivative thereof. According to the invention, a pharmaceutically acceptable derivative includes, but is not limited to, pharmaceutically acceptable salts, esters, salts of such esters, or any other adduct or derivative which upon administration to a subject in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an active metabolite or residue thereof. As used herein, the term "active metabolite or residue thereof" means that a metabolite or residue thereof is also an EGFR TKI.

Pharmaceutically acceptable salts are well known in the art. For example, S. M. Berge, et al., describe pharmaceutically acceptable salts in detail in J. Pharmaceutical Sciences, 1977, 66, 1-19, incorporated herein by reference. Pharmaceutically acceptable salts include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counter-ions such as halide, hydroxide, carboxylate, sulfate, phosphate, nitrate, lower alkyl sulfonate and aryl sulfonate.

Polymorphism, the occurrence of different crystal forms, is a property of some molecules and molecular complexes. A single molecule, like erlotinib, may give rise to a variety of crystalline forms having distinct crystal structures and physical properties like melting point, x-ray diffraction pattern, infrared absorption fingerprint, and solid state NMR spectrum. One crystalline form may give rise to thermal behavior different from that of another crystalline form. Thermal behavior can be measured in the laboratory by such techniques as capillary melting point, thermogravimetric analysis ("TGA"), and differential scanning calorimetry ("DSC"), which have been used to distinguish polymorphic forms. The difference in the physical properties of different crystalline forms results from the orientation and intermolecular interactions of adjacent molecules or complexes in the bulk solid. Accordingly, polymorphs are distinct solids sharing the same molecular formula yet having distinct advantageous physical properties compared to other crystalline forms of the same compound or complex.

All forms of erlotinib or a pharmaceutically acceptable salt thereof are intended to be within the scope of the present invention.

Although it is possible to administer the compound of the present invention in the form of a bulk active chemical, it is preferred to administer the compound in the form of a pharmaceutical composition or formulation. Thus, one aspect the present invention includes pharmaceutical compositions comprising erlotinib and/or pharmaceutically acceptable salts thereof and one or more pharmaceutically acceptable carriers, diluents, or excipients.

The manner in which the compound of the present invention is administered can vary. The compound of the present invention is preferably administered orally. Preferred pharmaceutical compositions for oral administration include tablets, capsules, caplets, syrups, solutions, and suspensions. The pharmaceutical compositions of the present invention may be provided in modified release dosage forms such as time-release tablet and capsule formulations.

The compounds of the present invention may be used in the treatment of a variety of disorders and conditions and, as such, may be used in combination with a variety of other suitable therapeutic agents useful in the treatment or prophylaxis of those disorders or conditions.

As used herein, the terms "pharmaceutically acceptable composition" or "pharmaceutical composition" refer to erlotinib or a pharmaceutically acceptable salt thereof optionally admixed with one or more pharmaceutically acceptable carriers, diluents, or excipients. Pharmaceutically acceptable compositions preferably exhibit a degree of stability to environmental conditions so as to make them suitable for manufacturing and commercialization purposes.

Pharmaceutically acceptable compositions may comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. As an example, Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with erlotinib or a pharmaceutically acceptable salt thereof, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil;

olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutically acceptable compositions can be administered to humans and other animals orally, rectally, parenterally, intracisternally, intravaginally, intraperitoneally, topically (as by powders, ointments, or drops), bucally, as an oral or nasal spray, or the like.

Liquid dosage forms for oral administration include, but are not limited to, pharmaceutically acceptable emulsions, microemulsions, solutions, suspensions, syrups and elixirs. In addition to the active compound(s), a liquid dosage form may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid may be incorporated in an injectable product. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

Erlotinib or a pharmaceutically acceptable salt thereof may be formulated using nanotechnology. Nanoparticles are attractive for medical purposes based on their unique features, such as their surface to mass ratio being larger than that of other particles, their quantum properties, and their ability to adsorb and carry other compounds. Nanoparticles may have dimensions below 0.1 μm or 100 nm. Alternatively, a pharmaceutical composition may comprise relatively large (size>100 nm) nanoparticles, as needed for loading a sufficient amount of drug onto the particles. In addition, for drug delivery, not only engineered particles may be used as carrier, but also the drug itself may be formulated at a nanoscale, and then function as its own carrier. The composition of the engineered nanoparticles may vary. Source materials may be of biological origin like phospholipids, lipids, lactic acid, dextran, chitosan, or have more chemical characteristics like various polymers, carbon, silica, and metals. Especially in the area of engineered nanoparticles of polymer origin there is a vast area of possibilities for the chemical composition. See, for example, Martins et al., *Nanoparticle Drug Delivery Systems: Recent Patents and Applications in Nanomedicine*, Recent Patents on Nanomedicine, 2013, 3(2), pp. 1-14. Many cytotoxic chemotherapeutic agents have poor aqueous solubility.

These molecules are associated with poor physicochemical and biopharmaceutical properties, which makes the formulation difficult. One approach in this regard is the use of combination of cyclodextrin and nanotechnology in delivery system. See, for example, Gidwani et al., *A Comprehensive Review on Cyclodextrin-Based Carriers for Delivery of Chemotherapeutic Cytotoxic Anticancer Drugs*, BioMed Research International, Volume 2015, Article ID 198268, 15 pages. Cyclodextrins are chemically and physically stable macromolecules produced by enzymatic degradation of starch. They are water-soluble, biocompatible in nature with hydrophilic outer surface and lipophilic cavity. They have the shape of truncated cone or torus rather than perfect cylinder because of the chair conformation of glucopyranose unit. Cyclodextrins are classified as natural and derived cyclodextrins. Natural cyclodextrins comprise three well-known industrially produced (major and minor) cyclic oligosaccharides. The most common natural cyclodextrins are α, β, and γ consisting of 6, 7, and 8 glucopyranose units. They are crystalline, homogeneous, and nonhygroscopic substances. Amongst these, β-cyclodextrin is used for complexation due to perfect cavity size, efficient drug complexation and loading, availability, and relatively low cost. Various hydrophilic, hydrophobic, and ionic derivatives have been developed and utilized to improve the physicochemical and biopharmaceutical properties of drug and inclusion capacity of natural cyclodextrins. Hydroxypropyl-β-cyclodextrin (HP-β-CD), randomly methylated-β-cyclodextrin (RM-β-CD), and sulfobutylether-β-cyclodextrin (SBE-β-CD) are mostly preferred for complexation. Polymerized cyclodextrins are high molecular weight compounds, either water-soluble or insoluble. They offer the advantage of amorphous state and complexation without toxic effects. Examples of polymerized cyclodextrins are soluble anionic β-cyclodextrin polymer, soluble γ-cyclodextrin polymer, and epichlorohydrin β-cyclodextrin polymer. Cyclodextrin-based nanocarriers may be prepared by utilizing the concept of dual approach, which involves combination of two different approaches in a single delivery system. This covers two aspects firstly; the anticancer drug is complexed with suitable cyclodextrin and secondly encapsulation of complexed drug into carrier.

Erlotinib or a pharmaceutically acceptable salt thereof may also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compounds of this invention may be made by a variety of methods, including well-established synthetic methods. Illustrative general synthetic methods are set out below and then specific compounds of the invention are prepared in the working Examples. The compounds can be prepared according to the methods described below using readily available starting materials and reagents. In these reactions, variants may be employed which are themselves known to those of ordinary skill in this art but are not described in detail here.

Reference is made to U.S. RE 41,065 and incorporated herein by reference with regard to the description and synthesis of TARCEVA® (erlotinib hydrochloride).

EXAMPLES

Specific Example 1: Pulse-Continuous Erlotinib Results in Impressive Control of Central Nervous System Disease Based on evolutionary mathematical modeling data, the present inventors tested a novel schedule of twice weekly pulse erlotinib in combination with daily erlotinib as initial EGFR TKI treatment in patients with EGFR-mutant lung cancers.

The trial was a prospective, open-label, single center phase 1 dose-escalation study of twice weekly pulse dose and daily erlotinib in patients with EGFR-mutant lung cancers. The primary endpoint of the study was the identification of the maximum tolerated dose of the combination of twice weekly high dose and daily low dose erlotinib. Secondary endpoints included the measurement of progression-free survival, overall survival, complete and partial response rate, determination of central nervous system progression and pharmacokinetic analysis. The study was registered at clinicaltrials.gov (NCT01967095). The trial was conducted after approval from the institutional review board at Memorial Sloan Kettering. All patients provided written informed consent.

Patients had stage IV or recurrent EGFR-mutant lung adenocarcinomas and no prior treatment with an EGFR TKI. Prior cytotoxic chemotherapy was allowed. Patients were required to have measurable disease per RECIST (Response Evaluation Criteria in Solid Tumours), version 1.1). Patients must have had adequate organ function and a Karnofsky performance status of >70%, with reference to Karnofsky et al., *The Use of the Nitrogen Mustards in the Palliative Treatment of Carcinoma—with Particular Reference to Bronchogenic Carcinoma*, Cancer, 1948; 1(4):634-56. Patients with clinically stable brain metastases, either treated or untreated, were eligible.

Study Design

The study used a standard 3+3 dose escalation design. Three patients were enrolled at each dose level and assessed for 1 full cycle before a dose escalation decision was made. No intra-patient dose escalation was allowed. Cycle 1, week 1 (Days 1-7) consisted of pulse dose erlotinib on days 1 and 2 without daily low dose erlotinib on days 3 to 7. For all subsequent weeks, patients received pulse dose erlotinib on days 1 and 2, and erlotinib 50 mg oral daily for 5 days on days 3 to 7 which was repeated weekly to complete 21 day cycles. Cycle 1 was 4 weeks to account for one week of lead in pulse dose erlotinib only. For each dose level, the dose of pulse erlotinib on days 1-2 was escalated (supplemental Table 1).

Supplemental Table 1: Dose levels and the number of patients treated and any DLTs observed in the first cycle:

|  | Number treated | DLT |
|---|---|---|
| Dose level 1: 600 mg pulse | 3 | None |
| Dose level 2: 750 mg pulse | 3 | None |
| Dose level 3: 900 mg pulse | 3 | None |
| Dose level 4: 1050 mg pulse | 6 | 1 (grade 3 ALT/AST) |
| Dose level 5: 1200 mg pulse | 6 (+10 in expansion) | None |
| Dose level 6: 1350 mg pulse | 3 | 2 (grade 2 rash, grade 3 mucositis) |

Patients who did not experience a dose-limiting toxicity (DLT) continued treatment at the assigned dose until progression of disease, unacceptable toxicity, or withdrawal of informed consent. Dose reductions of the pulse dose were allowed for toxicity, in 150 mg increments.

Toxicity assessments: Patients were assessed five times during cycle 1 (28 days) and then every 21 days thereafter. Patient history, physical examination, complete blood count and serum chemistries were performed at each visit. Toxicity was graded according to the National Cancer Institute Common Terminology Criteria for Adverse Events (NCI CTCAE), version 4. Dose-limiting toxicity was defined as any grade 4 hematologic toxicity lasting greater than 5 days. Grade 3 thrombocytopenia with clinically significant bleeding was considered a DLT. All grade 3 or greater non-hematologic toxicities were considered DLTs with diarrhea, nausea and vomiting needing to be grade 3 for 72 hours despite maximal supportive care to qualify as a DLT. Once the maximum tolerated dose (MTD) was determined, an additional ten patients were enrolled at the MTD.

Response assessments: Response to therapy was assessed by interval imaging every 6 weeks with a CT scan with response evaluated per RECIST 1.1. After six cycles on treatment, patients could reduce the radiographic assessments to every 4 cycles (12 weeks).

Pharmacokinetic analysis: Whole-blood samples for plasma were collected at prescheduled time points for pharmacokinetic (PK) analysis. Plasma levels of erlotinib were determined using a validated liquid chromatography-tandem mass spectrometry assay. LC-MS/MS was performed using a Phenomenex Kinetex 2.6 μm core-shell Biphenyl column (50×3 mm) and Shimadzu HPLC. MS detection was using an AB SCIEX API 4000 triple quadrupole mass spectrometer operating in positive ion electrospray ionization (ESI) mode. Standard PK parameters were calculated using a noncompartmental method (WiNNonlin, Pharsight).

Statistical Analysis: Descriptive statistics were used to summarize the clinical characteristics of the patients. Progression-free survival was estimated using the Kaplan-Meier method, and defined as the time from start of study therapy until progression or death. Patients who did not experience the event of interest were censored at the date they came off study or date of last assessment if still receiving study therapy. Response rates were calculated using binomial proportions and exact 95% CIs. All statistical analyses were performed using R 3.2.2 (R Development Core Team) including the "survival" and "Hmisc" packages.

Results 34 patients were enrolled onto this study, including 24 patients on the dose escalation portion of the phase 1 study and 10 patients in an expansion cohort at the MTD. In total, sixteen patients were treated at the MTD. The clinical characteristics of all patients are listed in Table 1.

TABLE 1

| Patient characteristics Patient Characteristics | | |
|---|---|---|
| Age, Median (range) | | 61 (33-77) |
| Sex | | |
| Female | | 18 |
| Male | | 16 |
| KPS (%) | | |
| 90-100 | | 16 |
| 80 | | 15 |
| 70 | | 3 |
| Smoking status | | |
| Former (pack-yr range) | | 12 (<1-35) |
| Never | | 22 |
| EGFR sensitizing mutation | | |
| L858R | | 12 |
| Exon 19 deletion | | 21 |
| G719A | | 1 |
| Prior therapy | | |
| Yes | | 5 |
| No | | 29 |
| CNS involvement at diagnosis | | |
| Yes | | 11 |
| Treated | 5 | |
| WBRT | | 3 |
| SRS | | 1 |
| Craniotomy | | 1 |
| Untreated | 6 | |
| No | | 22 |

Eleven patients (32%) had brain metastases at diagnosis, 5 of whom received treatment (surgery or radiation) for their CNS disease prior to study enrollment.

Determination of the maximum tolerated dose: There were no DLTs seen at dose levels at the 600, 750 and 900 mg pulse dose levels. At the erlotinib 1050 mg pulse dose, there was one DLT of grade 3 transaminitis (Supplemental Table 1, above).

At 1350 mg pulse dose level, there were two DLTs: grade 3 rash and grade 3 mucositis. We then enrolled an additional three patients on to the 1200 mg erlotinib pulse dose level with no DLTs seen. The 1200 mg pulse on days 1 and 2 and 50 mg erlotinib on days 3 to 7 was determined to be the MTD.

Adverse events: All 34 patients were evaluable for toxicity (Table 2). No grade four or five toxicities were reported with no deaths on study. Most drug-related toxicities were grade 1 and 2. The most common (>25%) drug-related adverse events were rash, diarrhea, nausea, fatigue, mucositis, pruritus, vomiting, increased bilirubin and dry skin (Table 2). Of the sixteen patients treated at the MTD, only three of sixteen required a dose reduction of the pulse dose erlotinib; the reasons for dose reduction were grade 3 rash, intolerable grade 2 rash and intolerable grade 2 diarrhea. All three patients eventually were lowered to erlotinib 900 mg as the pulse dose. Six patients were removed from the study for toxicity: hyperbilirubinemia (1), possible pneumonitis (1), diarrhea (2), transaminitis (1) and mucositis (1).

TABLE 2

Study drug-related adverse events seen in ≥10% of patients

| Adverse Event | Grade 1 | Grade 2 | Grade 3 | Grade 4 | Total (any grade) |
|---|---|---|---|---|---|
| Rash | 21 (62%) | 8 (24%) | 1 (3%) | 0 | 30 (88%) |
| Diarrhea | 24 (71%) | 1 (3%) | 4 (12%) | 0 | 29 (85%) |
| Nausea | 10 (29%) | 3 (9%) | 2 (6%) | 0 | 15 (44%) |
| Fatigue | 8 (24%) | 4 (12%) | 0 | 0 | 12 (35%) |
| Mucositis | 8 (24%) | 3 (9%) | 1 (3%) | 0 | 12 (35%) |
| Pruritis | 11 (32%) | 0 | 0 | 0 | 11 (32%) |
| Vomiting | 9 (26%) | 1 (3%) | 1 (3%) | 0 | 11 (32%) |
| Bilirubin increased | 4 (12%) | 5 (15%) | 2 (6%) | 0 | 11 (32%) |
| Dry skin | 10 (29%) | 0 | 0 | 0 | 10 (29%) |
| ALT elevated | 6 (18%) | 1 (3%) | 1 (3%) | 0 | 8 (24%) |
| Alopecia | 7 (21%) | 0 | 0 | 0 | 7 (21%) |
| AST increased | 5 (15%) | 1 (3%) | 0 | 0 | 6 (18%) |
| Paronychia | 4 (12%) | 2 (6%) | 0 | 0 | 6 (18%) |
| Anorexia | 3 (9%) | 2 (6%) | 0 | 0 | 5 (15%) |
| Anemia | 2 (6%) | 1 (3%) | 1 (3%) | 0 | 4 (12%) |

Figure 2:
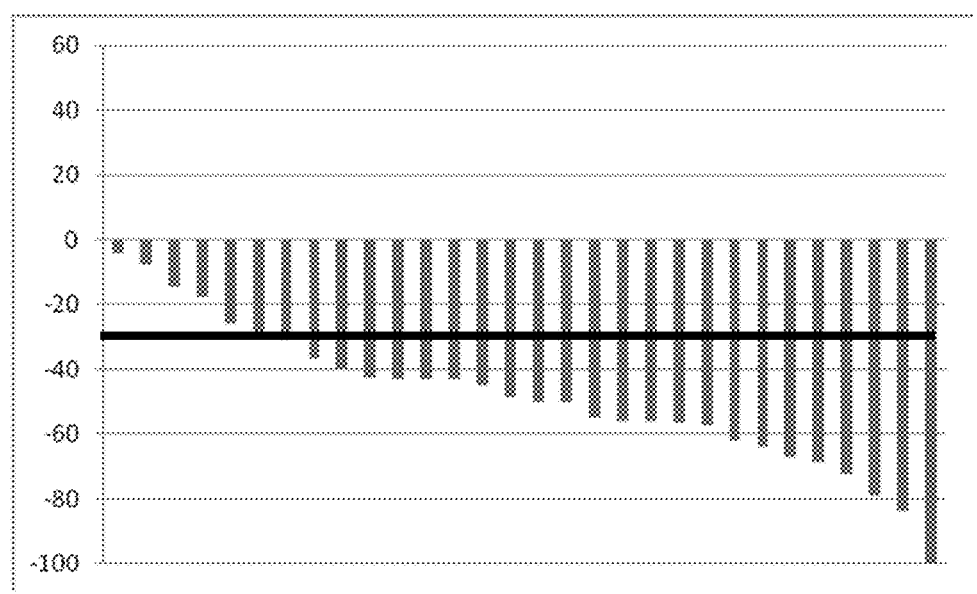
FIG. 2 is a graphical representation of best response of target lesions (RECIST 1.1) in all patients with a radiographic assessment of response.
Figure 3:
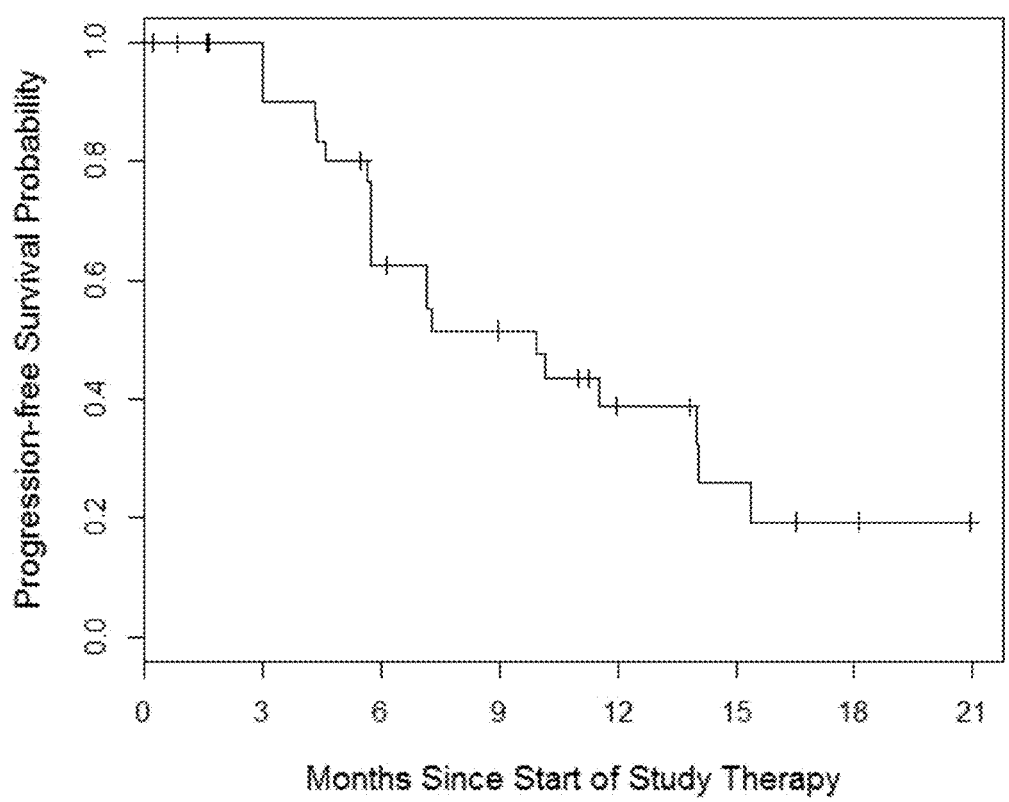
FIG. 3 is a graphical representation of progression-free survival probability from months since start of therapy.

Efficacy: All 34 patients were evaluable for response. Four patients came off study prior to the first follow-up radiographic assessment (3 due to toxicity, 1 due to non-compliance) and were counted as non-responders in our intent to treat analysis. Twenty-four patients had confirmed partial responses and one patient had a complete response (FIG. 2). The overall response rate was 74% (95% CI: 60-84%). All patients had a decrease in the sum of their target lesions. The maximum radiographic tumor change of target lesions for each patient with a follow up radiographic assessment is depicted in FIG. 2. The median progression-free survival is 9.9 months (95% CI 5.8-15.4 months) (FIG. 3). The overall survival estimate is not yet mature. Six subjects have died: four due to lung cancer progression, one due to Parkinson's disease and one due to a second primary gastric cancer.

Figure 4:
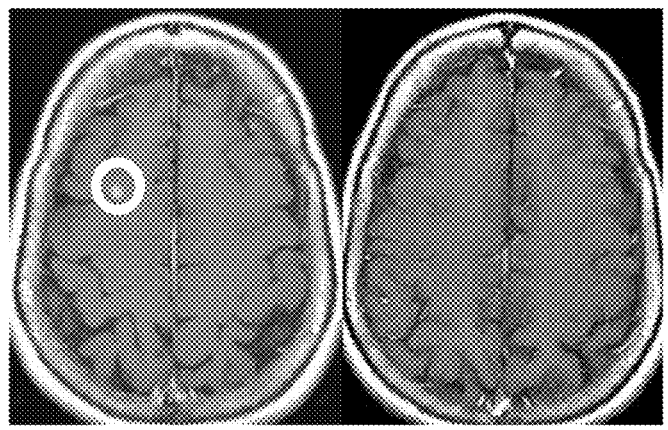
FIG. 4 is an example of CNS response in a patient with untreated brain metastases on the regimen, namely pulse-continuous erlotinib or a pharmaceutically acceptable salt thereof.
Figure 4:

Central nervous system activity: A brain MRI was required at enrollment. Eleven patients (32%) had brain metastases at study entry. No patient had leptomeningeal disease. Prior to the trial, 3 patients had whole brain radiation, 1 had stereotactic radiosurgery and 1 had a surgical resection. All 6 patients with untreated brain metastases had evidence of tumor regression in the CNS (FIG. 4). No patients had clinical CNS progression on study treatment. Of the 19 patients who came off study for progression of disease, 16 had CNS imaging within three months of coming off study and none had radiographic evidence of new or progressing brain metastases.

TABLE 3

Molecular findings at diagnosis and at acquired resistance for patients who came off study for progression

| | Baseline | | Acquired Resistance (off study for progression) | | |
|---|---|---|---|---|---|
| Pt | EGFR | Concurrent mutations | EGFR | T790M | Concurrent mutations |
| 1 | Ex19 del | Not done | Ex19 del | Positive | Not done |
| 2 | Ex19 del | Not done | Ex19 del | Positive | AURKA amp, GNAS amp, MEF2B gain, CCNE1 gain, AKT2 gain, MCL1 gain |
| 3 | Ex19 del | Not done | Ex19 del | Negative | CDK2NB del, CDKN2A del, BAP1 G109V, ETV1 R163Q, NOTCH3 G1689A |
| 4 | Ex19 del | Not done | Ex19 del | Positive | Not done |
| 5 | Ex19 del | Not done | Ex19 del | Positive | CCND2 amp, VEGFA amp, TERT gain, MDC1 gain, CDKN2B del, CDKN2A del, PAX5 del, AKT3 R166*, CSF1R A74T, INSR D1259A |
| 6 | L858R | Not done | L858R | Negative | Not done |
| 7 | L858R | Not done | L858R | Failed | Failed |
| 8 | L858R | Not done | L858R | Positive | TP53 M246V, APC S1100fs, BRIP1 I983fs, FBXW7 C573Y, RUNX1 ex5 del |
| 9 | Ex19 del | Not done | Ex19 del | Positive | Not done |
| 10 | Ex19 del | Not done | Ex19 del | Positive | Not done |
| 11 | Ex19 del | TP53 E298X, EGFR amp, MYC amp, RECQL4 amp, RB1 del, PDGFR R804Q, SETD2 N16343fs | Ex19 del | Positive | TP53 E298X, EGFR amp, ERBB2 amp, RAD21 amp, MYC amp, SDHA amp, TERT amp, IL7R amp, RICTOR amp, RECQL4 amp, RB1 del, PDGFR R804Q, SETD2 |
| 12 | Ex19 del | TP53 Q104X, EGFR amp, MYC amp, FLT1 R1146T, | Ex19 del | Positive | Failed |

TABLE 3-continued

Molecular findings at diagnosis and at acquired resistance
for patients who came off study for progression

| | Baseline | | Acquired Resistance (off study for progression) | | |
|---|---|---|---|---|---|
| Pt | EGFR | Concurrent mutations | EGFR | T790M | Concurrent mutations |
| 13 | Ex19 del | MCL1 G3S, PTPRD S569L Not done | Ex19 del | Positive | Failed |
| 14 | L858R | EGFR V689F, FGFR3 R399C, TP53 P36fs, AR G578X, ATRX S784F, BARD1 N73S, EPHA3 F152S, SMARCA4 P1277L | L858R | Negative | EGFR V689F, FGFR3 R399C, TP53 P36fs, AR G578X, ATRX S784F, BARD1 N73S, EPHA3 F152S, RET E164K |
| 15 | Ex19 del | Not done | Ex19 del | Positive | EGFR L747P, TP53 Y163N, PTEN F271S |
| 16 | Ex19 del | GNA11 R210L, TP53 C275W, PMS2 amp, RAC1 amp, EGFR amp, NKX2-1 amp, FOXA1 amp, PTEN del, GNAS K25N, RB1 ex10 SV, STAG2 D26E, TET1 | Ex19 del | Positive | GNA11 R210L, TP53 C275W, NKX2-1 amp, FOXA1 amp, CENPA E50fs, PLCG2 P999T, RB1 ex10 SV, STAG2 D26E, TET1 Q683P |
| 17 | Ex19 del | Not done | Ex19 del | Positive | PIK3CA E542K, TP53 V73fs, CCNE1 amp, EGFR amp, RICTOR gain, IL7R I121fs, MAP2K4 R304*, MLL3 D3461N |
| 18 | Ex19 del | Not done | Ex19 del | Positive | PIK3CA E542K, CTNNB1 S33F, LATS1 K652R, TGFBR2 K399fs |
| 19 | Ex19 del | PIK3CA E545K, TP53 ex5 del, EGFR gain, EPHB1 E144K, | Ex19 del | Negative | PIK3CA E545K, TP53 ex5 del, MET gain, EGFR gain, SETD2 T2316A |

Amp = amplification,
del = deletion

Mechanisms of acquired resistance: Of the nineteen patients that progressed on study therapy, six continued daily erlotinib at standard doses for >2 months after discontinuation of study therapy. Nineteen patients had a tumor biopsy at the time of progression. One patient's biopsy sample was inadequate for molecular analysis. Fourteen of eighteen (78%, 95% CI 54%-91%) patients had EGFR T790M identified in their rebiopsy specimen. Of the eighteen patients, eleven patients had next generation sequencing of their acquired resistance biopsy sample, and four had a paired pre-treatment tumor sample as well. Multiple concurrent mutations were found in both baseline and acquired resistance tumor samples in addition to the sensitizing EGFR mutation which was identified in all samples. Acquired molecular alterations not present in baseline samples included HER2 and MET amplification which have been previously reported (33, 34) as well as amplification in RAD21, SDHA, TERT, IL7R and RICTOR, and mutations in RET E164K, CENPA E50fs, and PLCG2 P999T.

Figure 5:
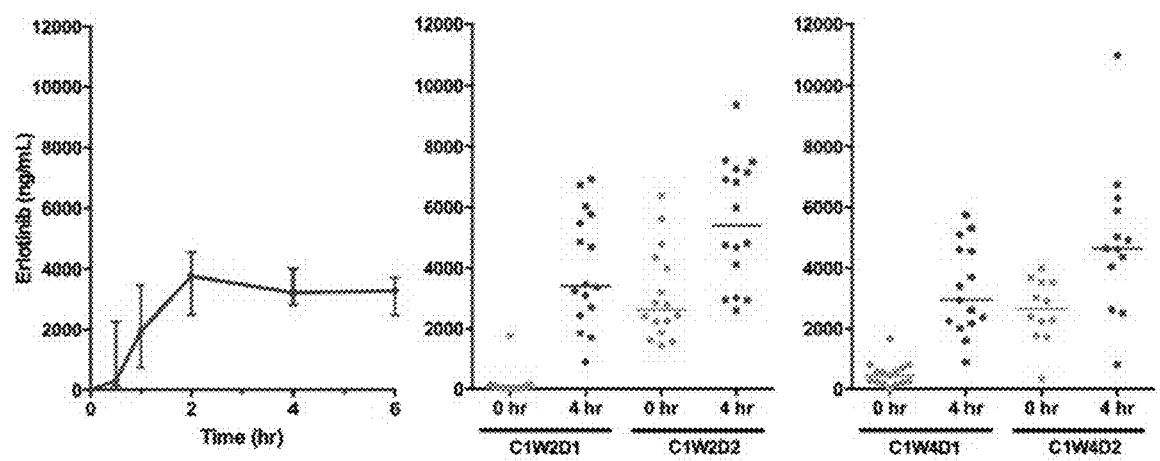
FIG. 5 is a graphical representation of plasma concentration curves for erlotinib after multiple dosing. Blood samples were collected during cycle 1 week 1 day 1 at 0.5, 1, 2, 4, and 6 hours after the first dose; before and four hours after erlotinib dosing on cycle 1 week 2 day 1 and cycle 1 week 4 day 1.

Pharmacokinetic analysis: Samples were collected from all 34 patients in the phase 1 study at the pre-specified time points. Median plasma concentration-time profiles are shown in FIG. 5. There was significant intra-patient variability in erlotinib plasma concentrations. No significant increase in peak plasma concentration was observed with increasing pulse doses of erlotinib from 600 mg to 1,350 mg, at any time point examined during Cycle 1. This was also confirmed by analysis of the major erlotinib drug metabolites (OSI-420 and M11), which showed no significant dose-dependence with increasing pulse doses of erlotinib. The peak plasma concentration occurred after the second day of weekly pulse dose at Week 2, with median plasma concentration at 4 hr post-administration reaching 5,393 ng/mL (range 2,600-9355 ng/mL), approximately 13.7 micromolar, more than 5 times the peak plasma concentration seen with standard 150 mg dosing (35). The median plasma trough concentration before the pulse dosing at the start of week 4 was 435 ng/mL (range: 29-1655 ng/mL), a concentration of 1.1 micromolar. This level at week 4 is consistent with 24 hr plasma concentrations observed following standard 150 mg dosing (35).

Patient disposition: six patients remain enrolled in the study. Nineteen patients discontinued study therapy because of progressive disease, and six others for adverse events discussed above. Two patients stopped study therapy due to non-compliance and one due to the development of an unrelated gastric adenocarcinoma.

We believe this is the first time evolutionary cancer modeling was used to optimize dosing of a targeted therapy. This dosing schedule derived from mathematical modeling did not delay the development of resistance or prevent the emergence of EGFR T790M despite validation in vitro and in vivo pre-clinical models. A likely explanation is that the peak plasma concentrations in patients may not have been high enough to correspond to the peak concentrations utilized in the pre-clinical models. The pulse and low dose concentrations used in the pre-clinical models were 20 micromolar and 1 micromolar, respectively. The median peak and trough concentration obtained at the MTD in our study was 13.7 micromolar and 1.1 micromolar, respectively. We were limited in exploring higher pulse dose levels due by toxicity resulting in DLTs. In addition, in the relatively few samples obtained in this phase 1 study (n=3-6 for dose levels 1-4 and 6), there were no significant increases in plasma peak concentration with increasing pulse doses from 600 mg to 1,350 mg, presumably due to limitations in drug absorption or due to drug clearance or metabolism. Even if toxicity were not an issue at higher dose levels, it is uncertain whether shorter dosing intervals or higher doses would result in the peak plasma concentrations required to delay EGFR T790M. The peak concentrations of erlotinib required to delay EGFR T790M do not appear achievable clinically. There are other potential limitations to our clinical model that may have contributed to our negative findings. The original modeling utilized both pulse afatinib and erlotinib, with the combination of pulse afatinib and daily erlotinib as superior at delaying resistance. Differences between erlotinib and afatinib may translate to disparate activity against EGFR T790M, and our results may have been different if we had utilized pulse afatinib. In addition, there are limitations inherent to any model system that considers multiple variables but cannot fully account for the entire complexity of all host and tumor factors.

Pulse-continuous erlotinib was well tolerated. The most common treatment related adverse events were rash, diarrhea, nausea, fatigue and mucositis. When compared to prospective studies of standard daily dosed erlotinib and afatinib, BR.21 and Lux-Lung 3, respectively, toxicity was similar. See, Sequist et al., *Phase III Study of Afatinib or Cisplatin Plus Pemetrexed in Patients With Metastatic Lung Adenocarcinoma With EGFR Mutations*, Journal of Clinical Oncology, 2013, 31(27):3327-34, and Shepherd et al., *Erlotinib in previously treated non-small-cell lung cancer*, The New England Journal of Medicine, 2005, 353(2):123-32.

Surprisingly, the study showed no significant increase in toxicity with pulse continuous erlotinib, despite a five times increase in the median peak plasma concentration of erlotinib compared to standard dosing. See, Hamilton et al., *Effects of smoking on the pharmacokinetics of erlotinib*, Clinical Cancer Research, 2006, 12(7 Pt 1):2166-71. Pulse dosing may result in decreased toxicity compared to the same amount of drug divided among daily doses, as toxicity may be related to drug trough or steady state concentrations, rather than peak concentrations.

This observation is corroborated by our previous study of once weekly pulse dose erlotinib at 2000 mg once weekly which also showed a similar toxicity profile to standard daily dose erlotinib. See, Milton et al., *A phase I/II study of weekly high-dose erlotinib in previously treated patients with nonsmall cell lung cancer*, Cancer, 2006, 107(5):1034-41. The present study demonstrates that pulse-continuous erlotinib is a feasible dosing schedule that is tolerated by most people.

The efficacy of pulse continuous erlotinib was similar to standard dose erlotinib for lung cancer. The overall response rate was 74% (95% CI 60-84%) and the median progression free survival was 9.9 months (95% CI 5.8-15.4 months). The dose and schedule of erlotinib assessed in this clinical trial did not improve response rates, prolong progression free survival or delay systemic resistance. The 78% (95% CI 54%-91%) frequency of EGFR T790M at the time of acquired resistance was comparable what is seen with standard dosing. Further study is needed to investigate whether drug dosing alters the mechanisms of resistance that emerge. Central nervous system metastases are a critical issue in the management of patients with EGFR-mutant lung cancers. Due to a prolonged disease course and improved overall survival, EGFR-mutant cancers may be enriched for CNS involvement with the cumulative incidence of CNS metastases approaching 60%. See, for example, Heon et al., *The impact of initial gefitinib or erlotinib versus chemotherapy on central nervous system progression in advanced nonsmall cell lung cancer with EGFR mutations*, Clinical Cancer Research, 2012, 18(16):4406-14; Omuro et al., *High incidence of disease recurrence in the brain and leptomeninges in patients with nonsmall cell lung carcinoma after response to gefitinib*, Cancer, 2005, 103(11):2344-8; Lee et al., Frequent central nervous system failure after clinical benefit with epidermal growth factor receptor tyrosine kinase inhibitors in Korean patients with nonsmall-cell lung cancer, Cancer, 2010, 116(5):1336-43; Heon et al., *Development of central nervous system metastases in patients with advanced non-small cell lung cancer and somatic EGFR mutations treated with gefitinib or erlotinib*, Clinical Cancer Research, 2010, 16(23):5873-82; Rangachari et al., *Brain metastases in patients with EGFR-mutated or ALK-rearranged non-small-cell lung cancers*, Lung Cancer, 2015, 88(1):108-11; and Kris et al., *Using Multiplexed Assays of Oncogenic Drivers in Lung Cancers to Select Targeted Drugs*, J. Am. Med. Assoc., 2014; 311(19):1998-2006.

Despite new treatments, such as osimertinib, that have demonstrated impressive systemic efficacy, CNS failures on treatment are common. In addition, patients with CNS involvement demonstrate lower response rate and shorter progression free survival with the 3rd generation EGFR TKIs compared to patients without CNS metastases. See, Camidge et al., *Activity of Rociletinib in EGFR Mutant NSCLC Patients With a History of CNS Involvement World Conference on Lung Cancer*, 2015, Oral presentation at the World Conference on Lung Cancer, Denver, CO.

This is believed to be the first demonstration of pretreatment incidence of CNS involvement in study subjects and also the rate of CNS progression on an EGFR TKI therapy. None of the prior large prospective studies of EGFR tyrosine kinase inhibitors include this information. See, for example, Rosell et al., *Erlotinib versus standard chemotherapy as first-line treatment for European patients with advanced EGFR mutation-positive non-small-cell lung cancer (EURTAC): a multicentre, open-label, randomised phase 3 trial*, The Lancet Oncology, 2012, 13(3):239-46; Sequist et al., *Phase III Study of Afatinib or Cisplatin Plus Pemetrexed in Patients With Metastatic Lung Adenocarcinoma With EGFR Mutations*, Journal of Clinical Oncology, 2013, 31(27):3327-34; Janne et al., *Randomized Phase II Trial of Erlotinib Alone or With Carboplatin and Paclitaxel in Patients Who Were Never or Light Former Smokers With Advanced Lung Adenocarcinoma: CALGB 30406 Trial*, Journal of Clinical Oncology, 2012, 39(17): 2063-9; Zhou et al., *Erlotinib versus chemotherapy as first-line treatment for patients with advanced EGFR mutation-positive non-small-cell lung cancer (OPTIMAL, CTONG-0802): a multicentre, open-label, randomised, phase 3 study*, The Lancet Oncology, 2011, 12(8):735-42; and Mitsudomi et al., *Gefitinib versus cisplatin plus docetaxel in patients with non-small-cell lung cancer harbouring mutations of the epidermal growth factor receptor (WJTOG3405): an open label, randomised phase 3 trial*, The Lancet Oncology, 2010, 11(2): 121-8.

As site of failure has prognostic as well as treatment implications, the present inventors suggest the rate of CNS failure be explicitly reported in all future prospective studies in lung cancers. Within EGFR-mutant lung cancers, understanding the CNS efficacy of drugs is critically important and will help in the selection between and among drugs that may have similar systemic effect.

The pulse continuous erlotinib dosing resulted in response in pre-existing brain metastases and prevention of new brain metastases while on treatment. Using retrospective data, CNS progression with or without concurrent systemic progression can occur in up to 33% of patients treated with standard dosing of EGFR TKI, with isolated CNS progression in up to 19% of cases. Heon et al., *The impact of initial gefitinib or erlotinib versus chemotherapy on central nervous system progression in advanced non-small cell lung cancer with EGFR mutations*, Clinical Cancer Research, 2012, 18(16):4406-14; Omuro et al., *High incidence of disease recurrence in the brain and leptomeninges in patients with nonsmall cell lung carcinoma after response to gefitinib*, Cancer, 2005, 103(11):2344-8; and Lee et al., *Frequent central nervous system failure after clinical benefit with epidermal growth factor receptor tyrosine kinase inhibitors in Korean patients with nonsmall-cell lung cancer*, Cancer, 2010, 116(5):1336-43.

The present data suggests that the CNS efficacy of this dosing schedule may be superior. The pulse continuous dosing allows for increased CNS penetration but continued daily dosing maintains systemic control of disease.

In summary, this is the first prospective study to assess an alternative dosing of an approved tyrosine kinase inhibitor based on evolutionary modeling. The regimen was well tolerated with a similar toxicity profile to standard dose erlotinib. Pulse continuous erlotinib did not lengthen progression-free survival or prevent the emergence of EGFR T790M as was hypothesized, perhaps due to the inability to achieve high enough plasma concentrations with the pulse doses used in this study. Surprisingly, however, none of the patients on study had evidence of new or progressing CNS disease on this regimen.

Specific Example 2—Adjuvant Therapy

Adjuvant therapy or care, also called adjunct therapy or adjunctive therapy or care, is therapy that is given in addition to the primary, main, or initial therapy to maximize its effectiveness. As an adjuvant agent modifies the effect of another agent, so adjuvant therapy modifies other therapy.

For example, resectable non-small-cell lung cancer (NSCLC) accounts for 20% to 25% of lung cancer cases diagnosed annually; however, only 60% of patients survive 5 years after surgery. The first trial to demonstrate a significant survival benefit with adjuvant cisplatin-based chemotherapy was reported a decade ago. Subsequently, additional randomized trials confirmed the role of adjuvant chemotherapy in patients with pathologic stage II and III NSCLC, and subset analyses suggested a benefit in patients with large IB tumors. A meta-analysis provided further support for adjuvant chemotherapy. Kelly et al., *Adjuvant Erlotinib Versus Placebo in Patients With Stage IB-IIIA Non-Small-Cell Lung Cancer (RADIANT): A Randomized, Double-Blind, Phase III Trial*, Journal of Clinical Oncology, Published Ahead of Print on Aug. 31, 2015 as 10.1200/JCO.2015.61.8918, sets forth a study design, patient population, assignment and masking protocol, study assessment, outcomes, and statistical analysis that could be used for a study of adjuvant efficacy. As such, that reference is incorporated herein in its entirety for such purpose. As set forth in Kelly et al., id, the signal of activity observed with erlotinib in patients with EGFR-expressing tumors combined with its oral availability and mild nonhematologic toxicity profile led to its evaluation in earlier stages of lung cancer. The Randomized Double-Blind Trial in Adjuvant NSCLC With Tarceva (RADIANT) study evaluated whether erlotinib would increase disease-free survival (DFS) in patients with completely resected stage IB to IIIA NSCLC whose tumors express EGFR.

As a further reference for conducting an adjuvant trial, Pennell et al., *SELECT: A Multicenter Phase II Trial of Adjuvant Erlotinib in Resected Early-stage EGFR Mutation-positive NSCLC*, presented at the 2014 ASCO meeting, provides study design, statistical considerations, patient characteristics, disease characteristics, treatment durations, dose monitoring, and outcomes and is hereby incorporated by reference in its entirety for such purpose.

The specific pharmacological responses observed may vary according to and depending on the particular active compound selected or whether there are present pharmaceutical carriers, as well as the type of formulation and mode of administration employed, and such expected variations or differences in the results are contemplated in accordance with practice of the present invention.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

What is claimed is:

1. A method for controlling formation of leptomeninges lesions in a patient with non-small cell lung cancer (NSCLC) that harbors an epidermal growth factor receptor (EGFR) mutation with pre-existing leptomeningeal metastases, the method comprising:
   a) orally administering to the patient:
      i) one or more pulse dose of erlotinib or a pharmaceutically acceptable salt thereof, wherein the pulse dose is between about 600 mg and about 1350 mg of erlotinib or a pharmaceutically acceptable salt thereof, wherein the one or more pulse dose of erlotinib or a pharmaceutically acceptable salt thereof is administered twice weekly; and
      ii) one or more daily dose of erlotinib or a pharmaceutically acceptable salt thereof, wherein the daily dose is from about 25 mg to about 50 mg of erlotinib or a pharmaceutically acceptable salt thereof; and
   b) administering to the patient one or more additional therapeutic compound, thereby controlling formation of leptomeninges lesions in the patient.

2. The method of claim 1, wherein the one or more additional therapeutic compound is an oncology therapeutic compound.

3. The method of claim 2, wherein the one or more additional therapeutic compound is an inhibitor of epidermal growth factor receptor (EGFR).

4. The method of claim 3, wherein the one inhibitor of EGFR is a mutant-selective inhibitor of EGFR.

5. The method of claim 1, wherein the one or more additional therapeutic compound is selected from the group consisting of rociletinib (CO-1686), osimertinib (AZD9291), HM61713, BI 1482694 and other third or later generation EGFR TKI.

6. The method of claim 1, wherein the pulse dose is administered once daily on each of days 1 and 2 of a weekly dosing schedule.

7. The method of claim 1, wherein the daily dose is administered once daily on each of days 3 to 7 of a weekly dosing schedule.

8. The method of claim 1, wherein the pulse dose is selected from the group consisting of 600 mg, 750 mg, 900 mg, 1050 mg, 1200 mg and 1350 mg of erlotinib or a pharmaceutically acceptable salt thereof.

9. The method of claim 1, wherein the daily dose is 50 mg of erlotinib or a pharmaceutically acceptable salt thereof.

10. The method of claim 1, wherein the patient experiences no tumor formation in the central nervous system.

11. The method of claim 1, wherein the patient's cerebrospinal fluid is cleared of malignant cells.

12. The method of claim 1, wherein the patient achieves an objective or complete response or disease control.

13. The method of claim 12, wherein the disease control is durable.

14. The method of claim 1, wherein the patient does not experience grade 4 or grade 5 toxicity.

15. The method of claim 1, wherein the patient experiences grade 1 or grade 2 toxicity.

16. A method for controlling formation of malignant cells in the cerebrospinal fluid (CSF) in a patient with non-small cell lung cancer (NSCLC) that harbors an epidermal growth factor receptor (EGFR) mutation with pre-existing CSF metastases, the method comprising:
a) orally administering to the patient:
  i) one or more pulse dose of erlotinib or a pharmaceutically acceptable salt thereof, wherein the pulse dose is between about 600 mg and about 1350 mg of erlotinib or a pharmaceutically acceptable salt thereof, wherein the one or more pulse dose of erlotinib or a pharmaceutically acceptable salt thereof is administered twice weekly; and
  ii) orally administering to the patient one or more daily dose of erlotinib or a pharmaceutically acceptable salt thereof, wherein the daily dose is from about 25 mg to about 50 mg of erlotinib or a pharmaceutically acceptable salt thereof; and
b) administering to the patient one or more additional therapeutic compound, thereby controlling formation of malignant cells in the cerebrospinal fluid (CSF) in the patient.

17. The method of claim 16, wherein the one or more additional therapeutic compound is an oncology therapeutic compound.

18. The method of claim 17, wherein the one or more additional therapeutic compound is an inhibitor of epidermal growth factor receptor (EGFR).

19. The method of claim 18, wherein the one inhibitor of EGFR is a mutant-selective inhibitor of EGFR.

20. The method of claim 16, wherein the one or more additional therapeutic compound is selected from the group consisting of rociletinib (CO-1686), osimertinib (AZD9291), HM61713, BI 1482694 and other third or later generation EGFR TKI.

21. The method of claim 16, wherein the pulse dose is administered once daily on each of days 1 and 2 of a weekly dosing schedule.

22. The method of claim 16, wherein the daily dose is administered once daily on each of days 3 to 7 of a weekly dosing schedule.

23. The method of claim 16, wherein the pulse dose is 600 mg, 750 mg, 900 mg, 1050 mg, 1200 mg and 1350 mg of erlotinib or a pharmaceutically acceptable salt thereof.

24. The method of claim 16, wherein the daily dose is 50 mg of erlotinib or a pharmaceutically acceptable salt thereof.

25. The method of claim 16, wherein the patient experiences no tumor formation in the central nervous system.

26. The method of claim 16, wherein the patient achieves an objective or complete response or disease control.

27. The method of claim 26, wherein the disease control is durable.

28. The method of claim 16, wherein the patient does not experience grade 4 or grade 5 toxicity.

29. The method of claim 16, wherein the patient experiences grade 1 or grade 2 toxicity.

\* \* \* \* \*